(12) United States Patent
Charest et al.

(10) Patent No.: US 9,784,396 B2
(45) Date of Patent: Oct. 10, 2017

(54) MICROFLUIDIC MANIFOLD FOR SHEAR SENSITIVE FLUIDS

(71) Applicant: The Charles Stark Draper Laboratory, Inc., Cambridge, MA (US)

(72) Inventors: Joseph L. Charest, Cambridge, MA (US); Jeffrey T. Borenstein, Newton, MA (US); Alla Epshteyn, Tampa, FL (US); Daniel I. Harjes, Acton, MA (US); Christopher DiBiasio, Stoughton, MA (US); Vijaya Kolachalama, Brookline, MA (US)

(73) Assignee: THE CHARLES STARK DRAPER LABORATORY, INC., Cambridge, MA (US)

(*) Notice: Subject to any disclaimer, the term of this patent is extended or adjusted under 35 U.S.C. 154(b) by 57 days.

(21) Appl. No.: 14/624,247

(22) Filed: Feb. 17, 2015

(65) Prior Publication Data
US 2015/0233512 A1 Aug. 20, 2015

Related U.S. Application Data

(60) Provisional application No. 61/940,577, filed on Feb. 17, 2014.

(51) Int. Cl.
*F16L 41/02* (2006.01)
*A61M 1/16* (2006.01)
(Continued)

(52) U.S. Cl.
CPC ............ *F16L 41/02* (2013.01); *A61M 1/14* (2013.01); *A61M 1/1627* (2014.02);
(Continued)

(58) Field of Classification Search
CPC ............ B81C 1/00119; B81C 99/0085; B01L 3/502707
(Continued)

(56) References Cited

U.S. PATENT DOCUMENTS 2,734,224 A * 2/1956 Winstead ............... B29C 47/14
118/410
3,585,131 A 6/1971 Esmond
(Continued)

FOREIGN PATENT DOCUMENTS

DE 68 01 138 U 3/1969
WO WO-2008/127732 A2 10/2008
(Continued)

OTHER PUBLICATIONS

International Preliminary Report on Patentability mailed Mar. 19, 2015 in PCT Application No. PCT/US2013/057842.
(Continued)

*Primary Examiner* — Craig Schneider
*Assistant Examiner* — Angelisa L Hicks
(74) *Attorney, Agent, or Firm* — Foley & Lardner LLP; Christopher J. McKenna

(57) ABSTRACT

A microfluidic device is provided. A manifold having a first channel, a second channel, and a third channel configured to transport blood can be coupled to a substrate defining an artificial vasculature. The first channel can be configured to carry blood in a first direction. Each of the second and third channels can couple to the first channel at a first junction and can be configured to receive blood from the first channel. The second channel can be configured to carry blood in a second direction away from the first direction. The third channel can be configured to carry blood in a third direction away from the second direction. The first, second, and third channels can be non-coplanar.

15 Claims, 8 Drawing Sheets

(51) Int. Cl.
  *B29C 45/00* (2006.01)
  *B01D 63/08* (2006.01)
  *A61M 1/14* (2006.01)

(52) U.S. Cl.
  CPC ........ *B01D 63/088* (2013.01); *B29C 45/0055* (2013.01); *B29C 45/0062* (2013.01); *A61M 2205/0244* (2013.01); *A61M 2206/20* (2013.01); *A61M 2207/00* (2013.01); *B01D 2325/028* (2013.01); *B29C 2045/0058* (2013.01); *B29C 2045/0077* (2013.01)

(58) Field of Classification Search
  USPC .............................................. 137/561 A, 833
  See application file for complete search history.

(56) References Cited

U.S. PATENT DOCUMENTS

| | | |
|---|---|---|
| 3,695,445 A | 10/1972 | Esmond |
| 4,110,220 A | 8/1978 | Lavender |
| 4,980,054 A | 12/1990 | Lavender |
| 2002/0182241 A1 | 12/2002 | Borenstein et al. |
| 2003/0039169 A1 | 2/2003 | Ehrfeld et al. |
| 2003/0150806 A1 | 8/2003 | Hobbs et al. |
| 2005/0020557 A1 | 1/2005 | Johnson et al. |
| 2005/0167354 A1 | 8/2005 | Caze et al. |
| 2006/0136182 A1 | 6/2006 | Vacanti et al. |
| 2008/0093298 A1 | 4/2008 | Browning et al. |
| 2008/0251444 A1 | 10/2008 | Fendya et al. |
| 2009/0181200 A1 | 7/2009 | Borenstein et al. |
| 2009/0234266 A1 | 9/2009 | Solomon et al. |
| 2009/0269837 A1 | 10/2009 | Shevkoplyas et al. |
| 2009/0316972 A1 | 12/2009 | Borenstein et al. |
| 2010/0234678 A1 | 9/2010 | Pryor et al. |
| 2010/0267136 A1 | 10/2010 | Vacanti et al. |
| 2010/0274353 A1 | 10/2010 | Pryor et al. |
| 2010/0326916 A1 | 12/2010 | Wrazel et al. |
| 2011/0155667 A1 | 6/2011 | Charest et al. |
| 2011/0290113 A1 | 12/2011 | Borenstein et al. |
| 2011/0296903 A1 | 12/2011 | Cao et al. |

FOREIGN PATENT DOCUMENTS

| | | |
|---|---|---|
| WO | WO-2011/059786 A1 | 5/2011 |
| WO | WO-2011/150216 A1 | 12/2011 |

OTHER PUBLICATIONS

International Search Report and Written Opinion mailed Apr. 16, 2014 in PCT Application No. PCT/US2014/010440.
International Search Report and Written Opinion mailed Oct. 23, 2013 in PCT Application No. PCT/US2013/057842 (13 pages).
US Office Action in U.S. Appl. No. 13/604,256 DTD Nov. 18, 2014.
US Office Action issued Feb. 12, 2014 in U.S. Appl. No. 13/604,256 (21 pages).
US Office Action in U.S. Appl. No. 13/604,256 dated Apr. 6, 2015.
International Search Report and Written Opinion mailed May 21, 2015 in PCT Application No. PCT/US2015/016171.
Office Action issued in European Patent Application No. 13765553.6 dated Feb. 23, 2016.
US Notice of Allowance for U.S. Appl. No. 13/604,256 dated Feb. 16, 2016.
US Notice of Allowance for U.S. Appl. No. 13/604,256 dated Jan. 20, 2016.
US Office Action for U.S. Appl. No. 13/604,256 dated Oct. 23, 2015.
US Office Action for U.S. Appl. No. 13/736,685 dated Mar. 3, 2016.
US Office Action for U.S. Appl. No. 13/736,685 dated Sep. 4, 2015.
Notice of Allowance issued Jun. 22, 2016 in U.S. Appl. No. 13/736,685.
Notice of Allowance issued Nov. 3, 2016 in U.S. Appl. No. 13/736,685.
Office Action issued Dec. 16, 2016 in European Patent Application No. 13765553.6.

* cited by examiner

MICROFLUIDIC MANIFOLD FOR SHEAR SENSITIVE FLUIDS

CROSS-REFERENCE TO RELATED APPLICATIONS

This application claims priority to U.S. Provisional Patent Application No. 61/940,577 filed on Feb. 17, 2014 and titled "MICROFLUIDIC MANIFOLD FOR SHEAR SENSITIVE FLUIDS," which is herein incorporated by reference in its entirety.

BACKGROUND

Microfluidic medical devices for processing blood may be used to introduce oxygen or clear undesirable particles from the blood of a patient. These microfluidic devices can include blood distribution manifolds coupled to processing channels. The processing channels of the device may not all lie within a single plane. Distribution of blood to the non-coplanar processing channels can be accomplished by a plenum. However, plenums typically require large priming volumes and do not permit the ability to control distribution of flow to individual conduits. Alternatively, a series of manifolds each having distribution channels in a one plane may be used, but a single planar manifold is incapable of distributing blood to non-coplanar processing channels.

SUMMARY OF THE INVENTION

Aspects and implementations of the present disclosure are directed to systems and methods for introducing fluid to non-coplanar processing channels of a microfluidic device.

At least one aspect is directed to a microfluidic device. The microfluidic device can include a manifold. The manifold can include a first manifold channel, a second manifold channel, and a third manifold channel coupled to a substrate defining an artificial vasculature. The first manifold channel can be configured to carry blood in a first direction. Each of the second and third manifold channels can couple to the first manifold channel at a first junction and can be configured to receive blood from the first manifold channel such that a total blood flow rate through the second and third manifold channels is substantially the same as a blood flow rate through the first manifold channel. The second manifold channel can be configured to carry blood in a second direction away from the first direction. The third manifold channel can be configured to carry blood in a third direction away from the first direction. The first, second, and third manifold channels can be non-coplanar.

In some implementations, walls of the junction are defined by one of a Hicks-Henne bump function, a non-uniform rational basis spline, a cubic spline, a T spline, a point cloud, and a polynomial function. In some implementations, the first manifold channel is further configured to carry blood at a first wall shear rate. In some implementations, the second manifold channel is further configured to carry blood at a second wall shear rate, lower than the first wall shear rate. In some implementations, the third manifold channel is further configured to carry blood at a third wall shear rate, lower than the first wall shear rate.

In some implementations, the first junction is configured to ensure that a wall shear rate gradient through the junction is maintained below a threshold selected to maintain blood health. The threshold can be about 0.0006 inverse seconds per micron. In some implementations, the first manifold channel is configured to transport blood at a wall shear rate in the range of about 4500 inverse seconds to about 10,000 inverse seconds. In some implementations, at least one of the second manifold channel and the third manifold channel is configured to transport blood at a wall shear rate in the range of about 100 inverse seconds to about 800 inverse seconds. In some implementations, the first wall shear rate is selected to create a driving force sufficient to dislodge blood clots in the manifold.

In some implementations, the device includes fourth and fifth manifold channels. Each of the fourth and fifth manifold channels can couple to the second manifold channel at a second junction and can be configured to receive blood from the second manifold channel such that a total blood flow rate through the fourth and fifth manifold channels is substantially the same as a blood flow rate through the second manifold channel. The fourth manifold channel can be configured to carry blood in a fourth direction away from the second direction. The fifth manifold channel can be configured to carry blood in a fifth direction away from the second direction. The second, fourth, and fifth manifold channels can be non-coplanar.

In some implementations, the fourth manifold channel can be configured to carry blood at a fourth wall shear rate, lower than the second wall shear rate. The fifth manifold channel can be configured to carry blood at a fifth wall shear rate, lower than the second wall shear rate.

In some implementations, at least one of the first channel, the second channel and the third channel includes a transition region configured to change the wall shear rate experienced by blood transported through the at least one channel such that the wall shear rate experience by blood upstream from the transition region is higher than a wall shear rate experienced by blood downstream from the transition region. The transition region can include sidewalls defined by one of a Hicks-Henne bump function, a non-uniform rational basis spline, a cubic spline, a T spline, a point cloud, and a polynomial function. The cross-sectional area of the at least one channel upstream from the transition region can be larger than the cross-sectional area of the at least one channel downstream from the transition region. A length of the transition region can be selected to achieve a desired wall shear rate gradient in the transition region. In some implementations, the length of the transition region is inversely proportional to the wall shear rate gradient in the transition region.

In some implementations, the manifold further comprises sixth and seventh manifold channels that converge at a third junction to form an eighth manifold channel, such that a blood flow rate through the eighth channel is substantially the same as a total blood flow rate through the sixth and seventh manifold channels. The sixth channel can be configured to transport blood at a sixth wall shear rate. The seventh channel can be configured to transport blood at a seventh wall shear rate. The eighth channel can be configured to transport blood at an eighth wall shear rate, lower than both the sixth and seventh wall shear rates.

At least one aspect is directed to a method of manufacturing a microfluidic device. The method includes providing a first mold for a first portion of a manifold. The first portion can include a primary channel having an inlet and an outlet and configured to carry fluid in a first direction. The method includes injecting a polymer material into the first mold to form the first portion of the manifold. The method includes providing a second mold for a second portion of the manifold. The second portion can include a plurality of secondary channels. Each secondary channel can have an inlet and an outlet. The inlet of each secondary channel can couple to a first junction. The method includes injecting a polymer material into the second mold to form the second portion of the manifold. The method includes providing a third mold for a third portion of the manifold. The third portion can include a plurality of tertiary channels. Each tertiary channel can have an inlet and an outlet. The inlet of each tertiary channel can couple to a second junction. The method includes injecting a polymer material into the third mold to form the third portion of the manifold. The method includes fusing the first portion of the manifold to the second portion of the manifold such that the outlet of the primary channel couples to the inlets of each of the plurality of secondary channels at the first junction and the primary channel and the plurality of secondary channels are non-coplanar. The method includes fusing the second portion of the manifold to the third portion of the manifold such that the outlet of a first secondary channel couples to the inlets of each of the plurality of tertiary channels at the second junction and the first secondary channel and the plurality of tertiary channels are non-coplanar. In some implementations, the method includes polishing an inner surface of the manifold at the first junction and the second junction.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing.

DESCRIPTION OF CERTAIN ILLUSTRATIVE IMPLEMENTATIONS

Following below are more detailed descriptions of various concepts related to, and implementations of, systems and methods for introducing fluid to non-coplanar processing channels of a microfluidic device. The various concepts introduced above and discussed in greater detail below may be implemented in any of numerous ways, as the described concepts are not limited to any particular manner of implementation. Examples of specific implementations and applications are provided primarily for illustrative purposes.

Figure 1:
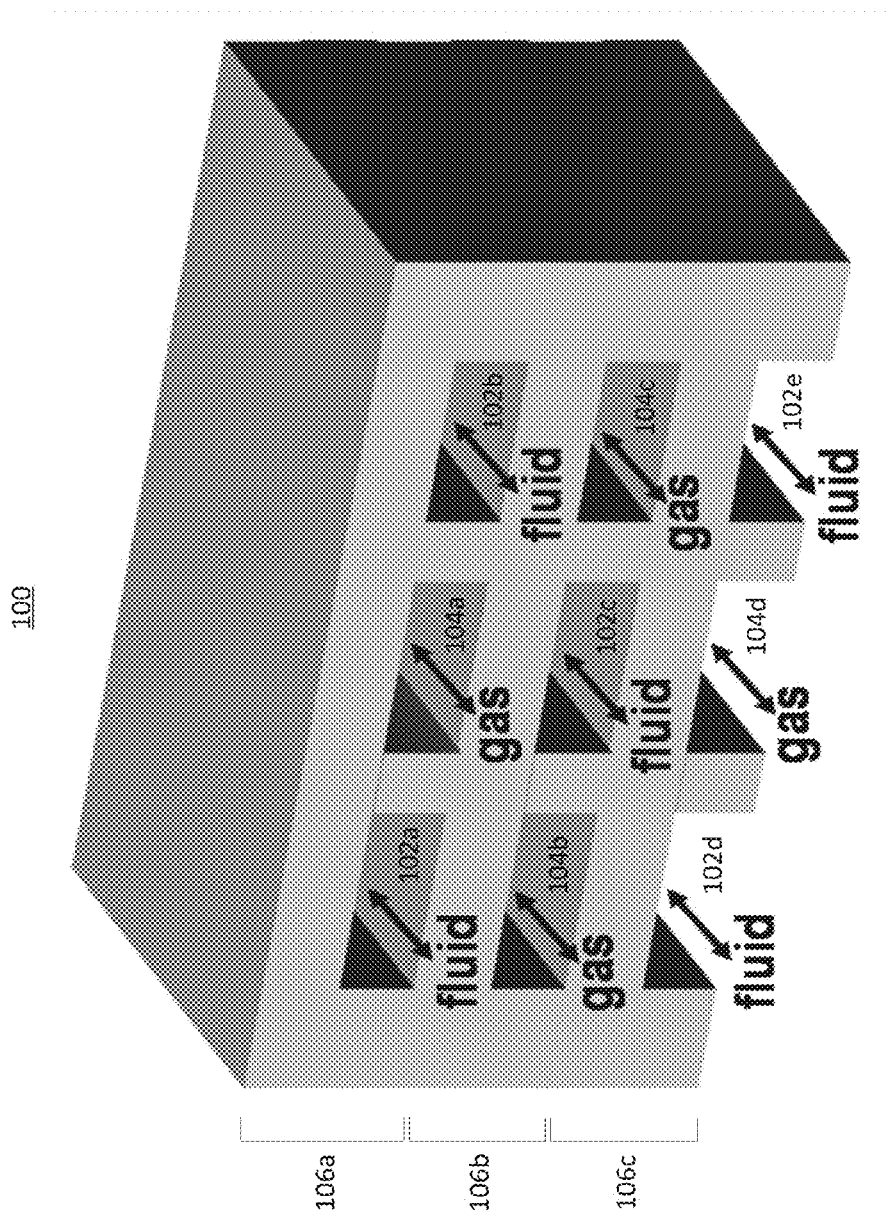
FIG. 1 is a cross-sectional view of a microfluidic device, according to an illustrative implementation.

FIG. 1 is a cross-sectional view of a microfluidic device 100, according to an illustrative implementation. The device 100 includes three layers 106a-106c (generally referred to as layers 106) that define fluid channels 102a-102e (generally referred to as fluid channels 102) and gas channels 104a-104d (generally referred to as gas channel 104). The channel ceilings, floors, and sidewalls are formed from a permeable material to facilitate gas exchange.

In some implementations, the device 100 can be used for facilitating gas exchange with a fluid. The microfluidic device 100 may be used in medical applications or industrial applications where it is desirable to transfer a gas to or from a fluid. For example, the microfluidic device 100 can be used in a lung assist device that supplements the function of a damaged lung in a patient by transferring oxygen to blood. As indicated by the arrows, fluid and gas flow in parallel directions in the channels 102 and 104. The device 100 is configured such that the channels within each layer 106 alternate between fluid channels 102 and gas channels 104. Furthermore, the layers 106 are arranged so that adjacent channels in different layers alternately carry fluid and gas. This configuration maximizes the surface area over which the fluid channels 102 interface with the gas channels 104 through the channel walls.

The channel walls are permeable to gas so that the gas flowing along the gas channels 104 can pass through to the adjacent fluid channels 102. The thickness of gas permeable material separating any gas channel 104 from an adjacent fluid channel 102 can be minimized so that gas can pass through the gas permeable material and into fluid in the fluid chamber 102. Features of the fluid channels 102, such as height, width, length, and shape can be optimized to maximize transfer of gas to and/or from a fluid, and also provide maintain healthy fluid flow properties for transmission of fluid, such as blood, through the device.

Fluid and gas can be introduced into the fluid channels 102 and gas channels 104 through respective manifolds. The fluid channels 102 and gas channels 104 are transverse to the front planar surface of the device 100, but not all of the fluid channels 102 and gas channels 104 are coplanar. Therefore, the manifolds used to introduce fluid into the fluid channels 102 and gas into the gas channels 104 are configured to carry fluid along conduits that are non-coplanar. In implementations in which the fluid is sensitive to changes in mechanical parameters including pressure or wall shear rate, such as when blood is transported through the fluid channels 102, the fluid manifold is also configured to maintain the fluid within a safe range of shear rates. The manifold used to introduce gas into the gas channels may not have the same requirements, as gas is typically not shear sensitive in most applications relevant to the device 100.

Figure 2A:
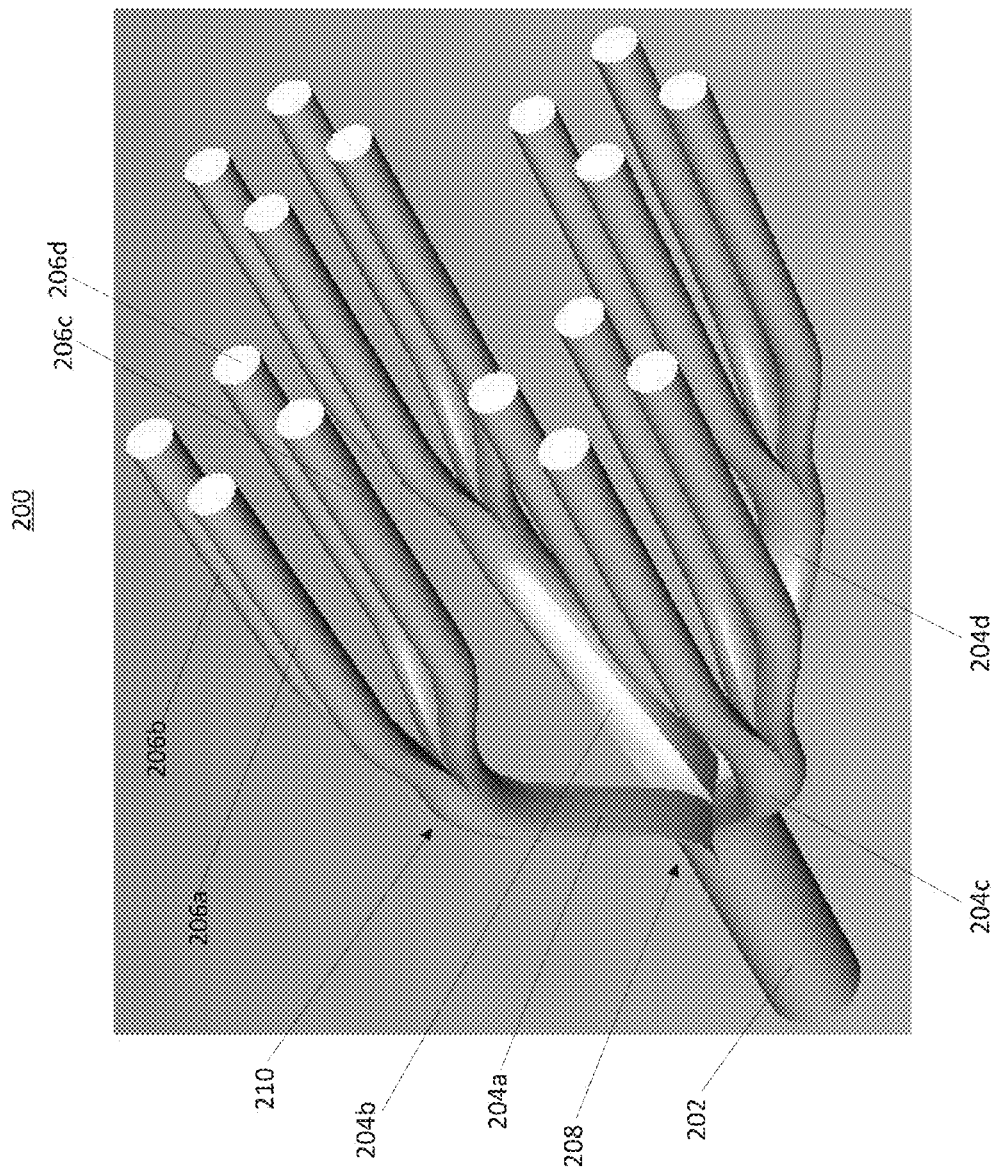
FIG. 2A is a depiction of a three-dimensional microfluidic manifold, according to an illustrative implementation.

FIG. 2A is a depiction of a three-dimensional microfluidic manifold 200, according to an illustrative implementation. The manifold 200 includes a primary channel 202, secondary channels 204a-204d (generally referred to as secondary channels 204), and tertiary channels such as tertiary channels 206a-206d (generally referred to as tertiary channels 206). In some implementations, the manifold 200 can be used in connection with the microfluidic device 100 shown in FIG. 1. For example, the manifold 200 can transport fluid, such as blood, into the fluid channels 102 shown in FIG. 1. FIG. 2A shows a solid representation of each of the channels in the manifold 200. In some implementations, the manifold 200 includes a solid structure that defines hollow channels corresponding to the channels shown in FIG. 2A. A depiction of such a manifold and a process for manufacturing the manifold is described further below in connection with FIGS. 4A-4C.

In some implementations, a volume of fluid enters the primary channel 202, for example via a pump that draws the fluid from a reservoir. As the fluid travels through the primary channel 202, it is redirected into the secondary channels 204 at the junction 208. Each of the secondary channels 204 is configured to carry fluid in a direction away from the primary channel 202. In addition, the secondary channels 204 are non-coplanar. That is, the manifold 200 is configured such that any combination of three secondary channels 204 are arranged to carry fluid in directions that do not lie within a single plane. The manifold 200 therefore branches out in three-dimensional space at the first junction 208.

Similarly, fluid traveling through the secondary channel 204a is redirected into the tertiary channels 206a-206d at the junction 210. Each of the tertiary channels 206 is configured to carry fluid in a direction away from the secondary channel 204, and the tertiary channels 206 are non-coplanar. The secondary channels 204b-204d also each include a junction at which the respective secondary channel 204 branches into tertiary channels 206.

The manifold 200 is illustrative only. For example, in some implementations, the manifold 200 may include more or fewer secondary channels 204. The secondary channels 204 may or may not be arranged with radial symmetry around an axis defined by the primary channel 202. In some implementations, the secondary channels 204 may be configured to evenly divide the fluid from the primary channel 202, each secondary channel 204 receiving an equal or substantially equal quantity of fluid from the primary channel 202. In other implementations, the secondary channels 204 can be configured to receive unequal portions of the fluid flowing through the junction 208. The percentage of fluid received by each secondary channel 204 can be controlled by varying the relative dimensions of each secondary channel 204. For example, a secondary channel 204 having a relatively large diameter can receive a larger percentage of fluid than a secondary channel 204 having a smaller diameter.

Likewise, the configuration of tertiary channels 206 shown in FIG. 2A is also illustrative, and other configurations are possible. For example, the junction 210 may include more or fewer tertiary channels 206 and the tertiary channels 206 may be configured to carry fluid in various directions away from the secondary channel 204a. In some implementations, the manifold may also include other features, such as quaternary channels formed at junctions located at the outlets of the tertiary channels 206.

In some implementations, the manifold 200 can be configured to maintain wall shear rates within ranges that are safe for the fluid used in a particular application. For example, manifold 200 can be configured to maintain wall shear rates in the range of about 100 to about 10,000 inverse seconds. The wall shear rate gradient can also be controlled to prevent abrupt changes in shear rate that may interfere with blood health. For example, in some implementations, the manifold is configured to transport blood such that shear rate gradients throughout the manifold 200 remain less than about 0.0006 inverse seconds per micron.

In some implementations, the primary channel 202, secondary channels 204, tertiary channels 206, and junctions 208 and 210 can be configured to control other mechanical parameters of fluid transported through the manifold 200. For example, the manifold 200 may be configured to maintain substantially laminar flow throughout the manifold 200 to limit cell rupture, reducing inflammation and coagulation of blood, limit the formation of blood clots, and prevent other damage to the blood. The manifold 200 can be configured to mimic a human vasculature. For example, the secondary channels 204 can have smaller diameters than the primary channel 202, and the tertiary channels 206 can have smaller diameters than the secondary channels 204. In some implementations, the diameter of an individual channel may taper along the length of the channel. In one example, the hydraulic diameters of the primary channel 202 and the secondary channels 204 are selected according to Murray's Law, which provides a technique for selecting the radius of channels in a network in order to balance the energy required to circulate fluid (e.g. blood) and the energy required to metabolically support the fluid. Generally, Murray's Law indicates that for a primary channel having a radius of $r_p$ and branch channels having radii of $r_{b1}$, $r_{b2}$, etc., the relationship between the radii of all of the channels should be: $r_p{}^3 = r_{b1}{}^3 + r_{b2}{}^3 + \ldots + r_{bn}{}^3$. Murray's Law can also be used to select the relationships between the hydraulic diameters of a primary channel and branch channels in a network with non-circular cross sections. For example, for a primary channel having a hydraulic diameter $d_p$ and branch channels having hydraulic diameters of $d_{b1}$, $d_{b2}$, etc., Murray's Law indicates that the relationship between the hydraulic diameters of all of the channels should be:

$$\left(\frac{dp1}{2}\right)^3 = \left(\frac{db1}{2}\right)^3 + \left(\frac{db2}{2}\right)^3 + \ldots + \left(\frac{dbn}{2}\right)^3$$

Murray's Law also can be used to select the angles at which the secondary channels 204 branch off from the primary channel 202, as well as the angles at which the tertiary channels 206 branch off from the secondary channels 204, in order to reduce the work required to circulate fluid through the manifold 200. For example, the angles of branching channels may be selected according to the following set of equations:

$$\cos(x) = \frac{r_p^4 + r_{b1}^4 - (r_p^3 - r_{b1}^3)^{4/3}}{2r_p^2 r_{b1}^2},$$

$$\cos(y) = \frac{r_p^4 + r_{b2}^4 - (r_p^3 - r_{b2}^3)^{4/3}}{2r_p^2 r_{b2}^2},$$

$$\cos(x+y) = \frac{(r_{b1}^3 + r_{b2}^3)^{4/3} - r_{b1}^4 - r_{b2}^4}{2r_{b1}^2 r_{b2}^2}$$

where $r_p$ is the radius of a primary channel 202 and the secondary channels 204 branching off of the primary channel 202 have radii of $r_{b1}$, $r_{b2}$, x is the angle at which the first secondary channel 204 having radius $r_{b1}$ branches from the primary channel 202, and y is the angle at which the second secondary channel 204 having radius $r_{b2}$ branches from the primary channel 202. It should be understood that these equations can also be used to select the dimensions and angles of tertiary channels 206 that branch from a secondary channel 204, for example by substituting the radius of the secondary channel 204 for $r_p$ and the radii of the tertiary channels 206 for the radii of $r_{b1}$ and $r_{b2}$. In some implementations, the tapering of each channel can be selected based in part on branching angles used for the channels in the manifold. Various cross-sectional shapes of the primary channel 202, secondary channels 204, and tertiary channels 206 may be selected, including triangular, rectangular, trapezoidal, or any other regular or irregular polygonal shape. In some implementations, the primary channel 202, secondary channels 204, and tertiary channels 206 may have cross-sectional shapes that include rounded or curved edges. For example, the primary channel 202, secondary channels 204, and tertiary channels 206 may have circular, semicircular, or elliptical shapes. In some implementations, the shape of the primary channel 202, the secondary channels 204, and the tertiary channels 206 may be defined as a central section of a conical cylinder having curvilinear walls. In some implementations, the manifold may include transitions from one cross-sectional shape to a different cross-sectional shape. Additional features that may be included in the manifold 200 are described further below in connection with FIGS. 4A-4B.

As described above, the manifold 200 can be used in connection with the device 100 of FIG. 1 to implement a lung assist device. Oxygen is transported through the gas channels 104 while blood is transported through the fluid channels 102 (via the manifold 200), and the blood is oxygenated by diffusion of oxygen through the channel walls. In some implementations, the manifold 200 can couple to an array of devices such as the device 100 of FIG. 1, with the entire array used to implement a single lung assist device. For example, the tertiary channels 206a-206d may couple to one instance of the device 100. The tertiary channels extending from secondary channel 204b may couple to a second instance of the device 100, the tertiary channels extending from secondary channel 204c may couple to a third instance of the device 100, and the tertiary channels extending from secondary channel 204d may couple to a fourth instance of the device 100. This arrangement can help to avoid excessive path lengths that would occur if the array of devices 100 were arrange linearly. In some implementations, the path length from the primary channel 202 through each tertiary channel 206 can be selected to be at least the minimum length required to achieve fully developed fluid flow. The dimensions of the manifold 200 as a whole can be selected based on the dimensions of the device, such as the device 100, to which the manifold 200 couples. For example, the manifold 200 may have a height approximately equal to the product of the height of the layers 106 of the device 100 and the number of layers 106 in the device. Likewise, the overall width of the manifold 200 can be approximately equal to the product of the width of the channels 102 of the device 100 and the number of channel 102 within each layer 106 of the device 100. In some implementations, the each of the channels in the manifold 200 may have a diameter in the range of about 50 microns to about 150 microns and a length in the range of about 0.5 centimeters to about 1.5 centimeters. In some implementations, the channels in the manifold 200 can have diameters of about 100 microns and lengths of about 1 centimeter. In some implementations, the manifold may have a rectangular profile. In other implementations, the manifold may have a different profile shape, such as a triangular or other polygonal shape.

Figure 2B:
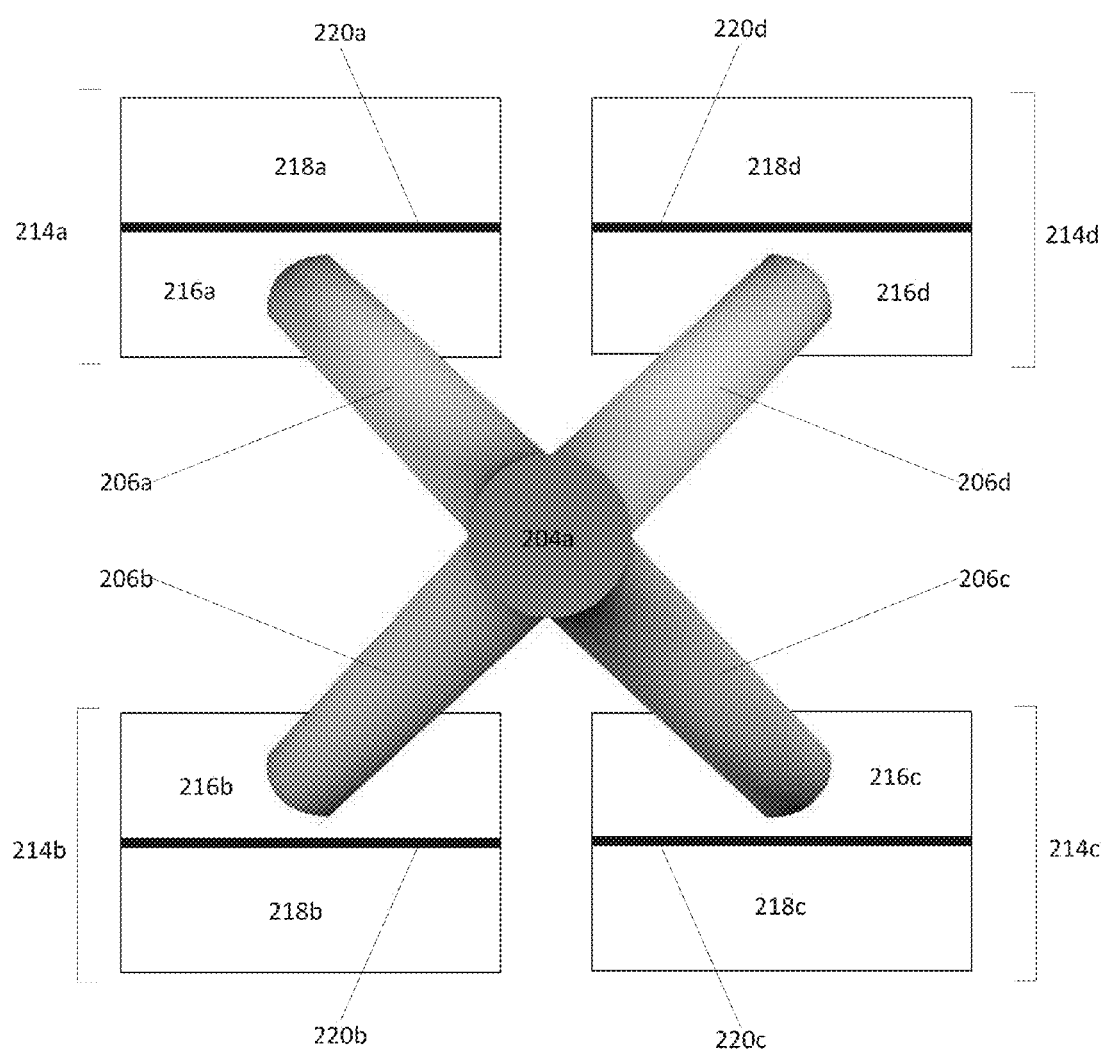
FIG. 2B is a depiction of a portion of the three-dimensional microfluidic manifold of FIG. 2A coupled to a hemofiltration device, according to an illustrative implementation

FIG. 2B is a depiction of a portion of the three-dimensional microfluidic manifold 200 of FIG. 2A coupled to a hemofiltration device, according to an illustrative implementation. The portion of the device 200 shown includes the secondary channel 204a and the tertiary channels 206a-206d. The device 200 is shown in cross-section, such that the secondary channel 204a and tertiary channels 206a-206d transport fluid in a direction that is substantially into the page on which they are drawn. The hemofiltration device includes four channel bilayers 214a-214d (generally referred to as channel bilayers 214). Each channel bilayer 214 includes a respective blood substrate layer 216a-216d (generally referred to as blood substrate layers 216) and a respective filtrate substrate layer 218a-218d (generally referred to as filtrate substrate layers 218) separated by a respective permeable membrane 220a-220d (generally referred to as membranes 220). The tertiary channels 206a-206d are coupled to the blood substrate layers 216a-216d, respectively. Each tertiary channel 206a-206d is configured to introduce blood into a network of blood flow channels within each blood substrate layer 216a-216d. In some implementations, one or more additional manifolds (not shown) can be used to introduce filtrate into the filtrate substrate layers 218.

The network of channels within the blood substrate layers 216 and the filtrate substrate layers 218 divide the fluid (i.e. blood and filtrate) into numerous channels so that a relatively large surface area of each fluid is exposed to the permeable membranes 220. Each channel of the blood substrate layers 216 can be aligned with a corresponding channel of the respective filtrate substrate layer 218, so that the corresponding channels are separated by the respective permeable membrane 220. In some implementations, a single filtrate channel may be separated from two or more blood channels by the permeable membrane 220. As the blood moves through the channels of the blood substrate layers 216, filtrate can flow in the opposite direction through the filtrate substrate layers 218 and waste products and water are removed from the blood via diffusion and convection through the permeable membrane 220 into the filtrate substrate layer 218. Healthy blood remains in the blood substrate layer 216 and can then be recirculated into the body of a patient after exiting through a blood outlet manifold (not shown). In some implementations, the blood outlet manifold can be or can include a manifold such as the manifold 200 shown in FIG. 2A.

As discussed above, the manifold 200 can have features that promote the health of blood transported through the manifold 200. As a result, the manifold 200 is useful for introducing blood into the blood substrate layers 216 because blood health can be preserved within the manifold 200 before it is transported into the blood substrate layers 200 for filtration. Although only a portion of the manifold 200 is shown in FIG. 2A, other portions (e.g., the remaining tertiary channels of the manifold) can be used to introduce blood into other blood substrate layers used to filter undesired particles from the blood. Because the manifold 200 can transport blood in non-coplanar directions through the tertiary channels 206, the channel bilayers 214 of the hemofiltration device can be arranged in an array of rows and columns, as shown in FIG. 2B. Such an arrangement can reduce the overall size of the hemofiltration device.

Figure 3A:
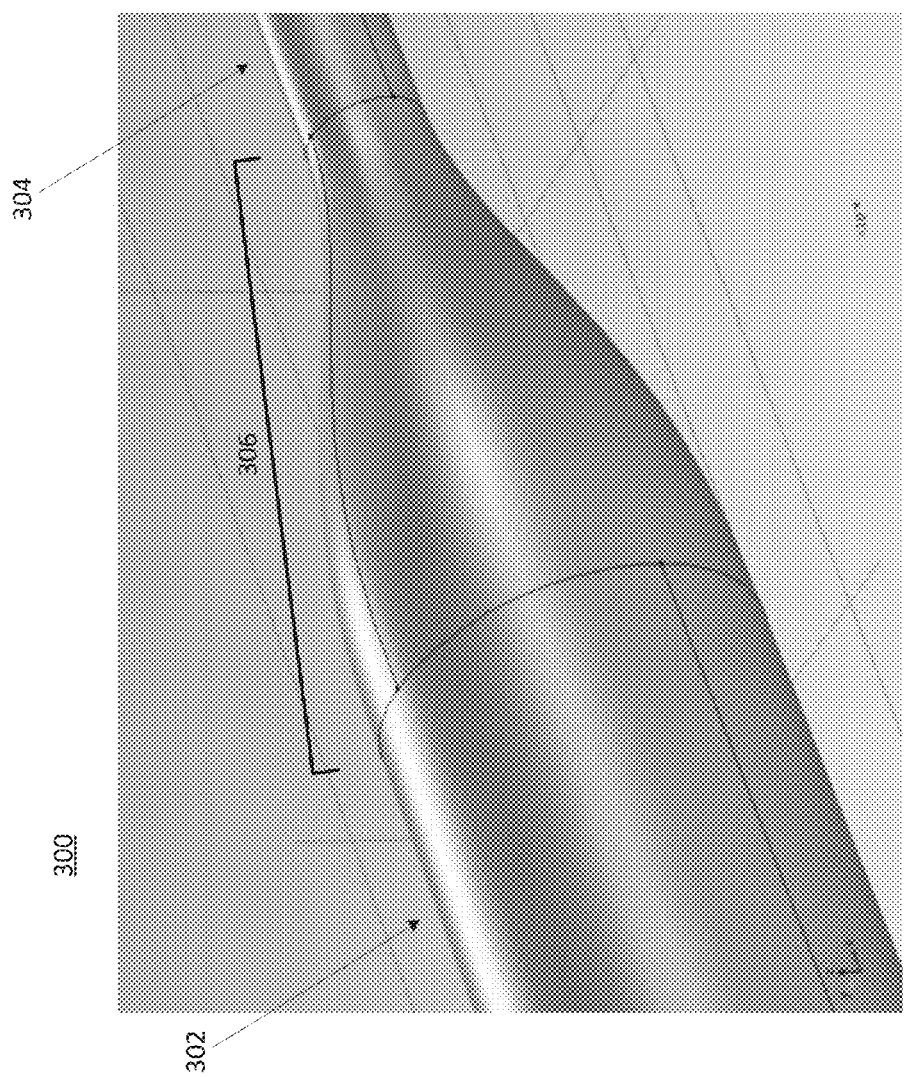
FIG. 3A is a depiction of a portion of a microfluidic channel that can be used to control a wall shear rate gradient, according to an illustrative implementation.

FIG. 3A is a depiction of a portion of a microfluidic channel 300 that can be used to control a wall shear rate transition, according to an illustrative implementation. The channel 300 includes an upstream region 302 and a downstream region 304 coupled by a transition region 306. The upstream region 302 and downstream region 304 are substantially cylindrical in shape, with the downstream region 304 having a diameter smaller than the diameter of the upstream region 302. The channel 300 can be used as a channel in the manifold 200 shown in FIG. 2A.

In some implementations, the channel 300 can be used to control the wall shear rate experienced by a fluid transported through the channel 300. For example, the shear rate in the upstream region 302 can be different from the shear rate in the downstream region 304, due to the difference in cross-sectional diameter of the two regions The upstream region 302 is substantially cylindrical. Therefore, the cross-sectional shape does not change along the length of the upstream region, and the shear rate at all points along the length of the upstream region 302 can remain substantially constant. Likewise, the downstream portion 304 is also substantially cylindrical and, as a result, can have a substantially constant shear rate along its length. The transition region 306 can be configured to maintain a well-defined wall shear rate at all points in the channel 300 between the upstream region 302 and the downstream region 304. Therefore, the shear rate can be defined for the entire length of the channel 300. Generally, the shear rate gradient in the transition region 306 can be inversely proportional to the length of the transition region 306. Channel regions with higher shear rates can have smaller volumes than regions with lower shear rates. For example, the downstream region 304 is configured to transport blood at a higher shear rate than the upstream region 302. To achieve the relatively higher shear rate, the downstream region 305 has a smaller cross-sectional area than the upstream region 302. As a result, the volume of the downstream region 304 over a given length is smaller than the volume of the upstream region 302 over the same length. Therefore, configuring the channel 300 to have a higher shear rate in the downstream portion can help to reduce the overall volume of the channel 300, while controlling the shear rate gradient in the transition region 306 allows blood health to be maintained throughout the channel 300. This and other benefits of including transition regions such as the transition region 306 in a microfluidic manifold are described further below.

In some implementations, the shape of the transition region can be defined by a mathematical function. Examples of suitable functions may include, but are not limited to, polynomial functions of any order, Hicks-Henne bump functions, non-uniform rational b-splines, cubic splines, T-splines, and Bezier curves. In some implementations, an approximation or modification of such a function may be used. For example, extrapolations or interpolations of functions or discretized versions of a function may be used. These modifications may facilitate the manufacturing in instances in which a manufacturing tool cannot form shapes that correspond exactly to a desired function.

FIG. 3A depicts a transition region 306 defined by the following fourth order polynomial:

$$f(x)=0.0045x^4-0.0292x^3-0.0071x^2+1.5$$

where the radius of the upstream region 302 is 1.5 millimeters, the radius of the downstream region 304 is 0.5 millimeters, and the function defines the radius along the length of the transition region 306. This particular polynomial is illustrative only. In other implementations, different coefficients may be used, or a polynomial function of a higher or lower order may be used. The wall shear rate in the transition region 306 can vary with the radius of the transition region 306. The function defining the shape of the transition region 306 may be selected to achieve a desired wall shear rate gradient. For example, the wall shear rate gradient can be maintained below a threshold of about 0.0006 inverse seconds per micron to preserve blood health.

Varying the wall shear rate at different points in the channel 300 can result in decreased priming volume when the channel 300 is used in a manifold such as the manifold 200 shown in FIG. 2A combined with a device such as the device 100 shown in FIG. 1. For example, while the shear rate may be required to remain within a specified range in the fluid channels 102 of the device 100 to facilitate oxygenation of the blood, maintaining the same shear rate in the manifold 200 may be unnecessary. Increasing the shear rate at some locations in the manifold 200 can result in a lower priming volume without decreasing the performance of the device 100. Using the transition region 306 to control the shear rate gradient between regions of higher shear (e.g., the upstream region 302) and regions of lower shear (e.g., the downstream region 304) can also protect blood from sharp changes in shear rate.

Increasing the shear rate in some portions of the channel 300 may also prevent clots from blocking the channel. For example, configuring the upstream portion 302 to transport fluid at a higher shear rate can also result in a higher fluid pressure in the upstream portion 302. The higher fluid pressure can create a driving force to dislodge clots before they are able to create blockages in the channel 300.

While FIG. 3A depicts the transition region 306 within a single channel 300, other types of transition regions may be used. For example, the junctions 208 and 210 shown in FIG. 2A may be configured to control wall shear rate gradients in the manifold 200. Principles similar to those discussed above can be applied to these junctions. The radius of the channel walls of the manifold can be tapered near the junctions according to a mathematical function chosen to provide a desired wall shear rate gradient. In other implementations, two or more channels upstream from a junction may merge into a single channel at the junction. The curvature of the channel walls near the merger point may be defined by a function to control the wall shear rate gradient.

Figure 3B:
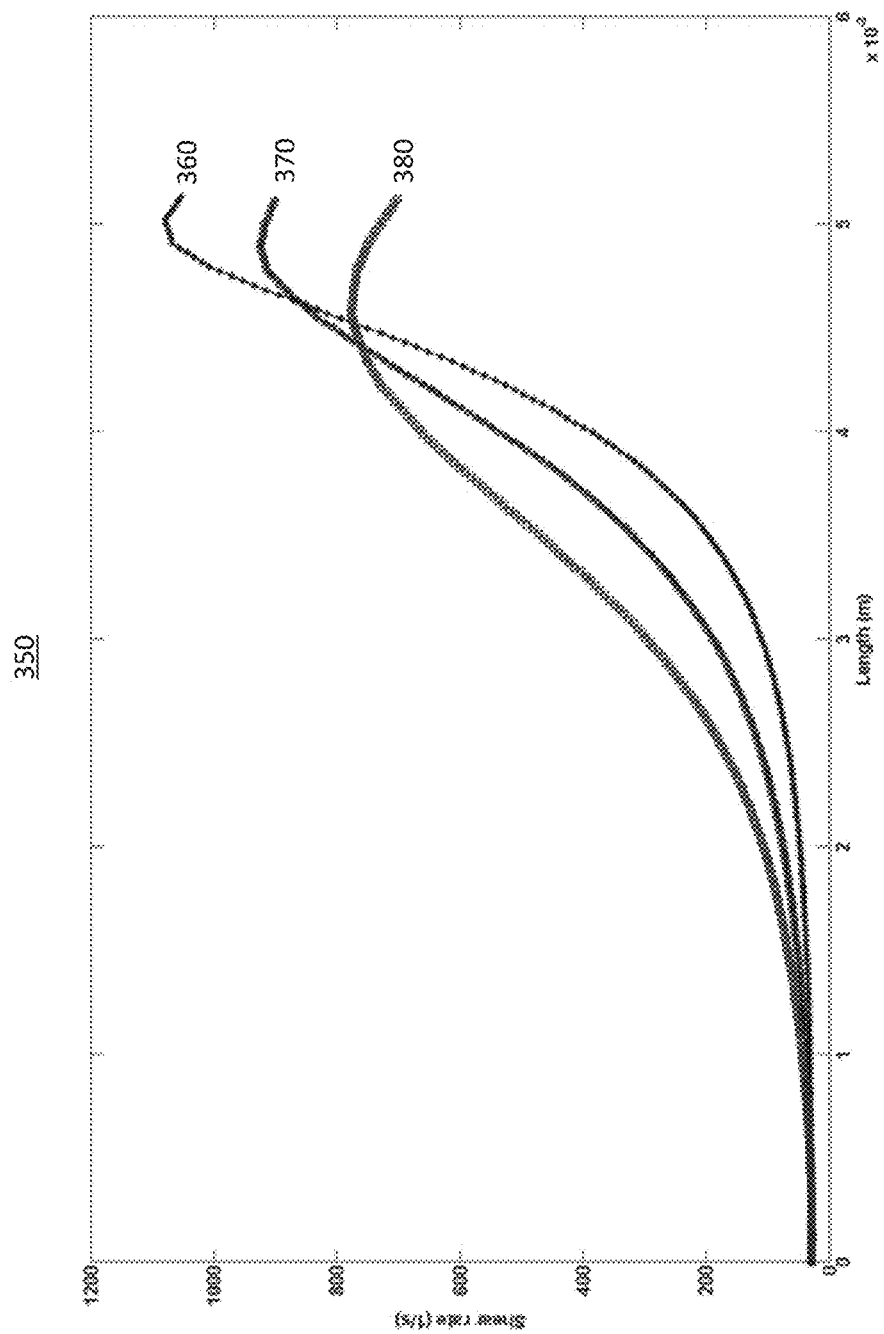
FIG. 3B is a graph of the shear rates along the length of various example microfluidic channels.

FIG. 3B is a graph 350 of shear rates along the lengths of various microfluidic channels. Line 360 shows represents the shear rate at in the transition region 306 of FIG. 3A. Line 370 represents the shear rates in a transition region defined by the following third order polynomial function:

$$f(x)=0.016x^3-0.12x^2+1.5$$

and line 380 represents the shear rates in a transition region defined by the following fourth order polynomial function:

$$f(x)=-0.0033x^4+0.0494x^3-0.2035x^2+1.5.$$

As shown, the shear rates of each transition region are characterized by smooth transitions over the entire length of the transition region. All of the transition regions maintain shear rates below a maximum of 1200 inverse seconds, which is a healthy shear rate for blood.

Figure 4A:
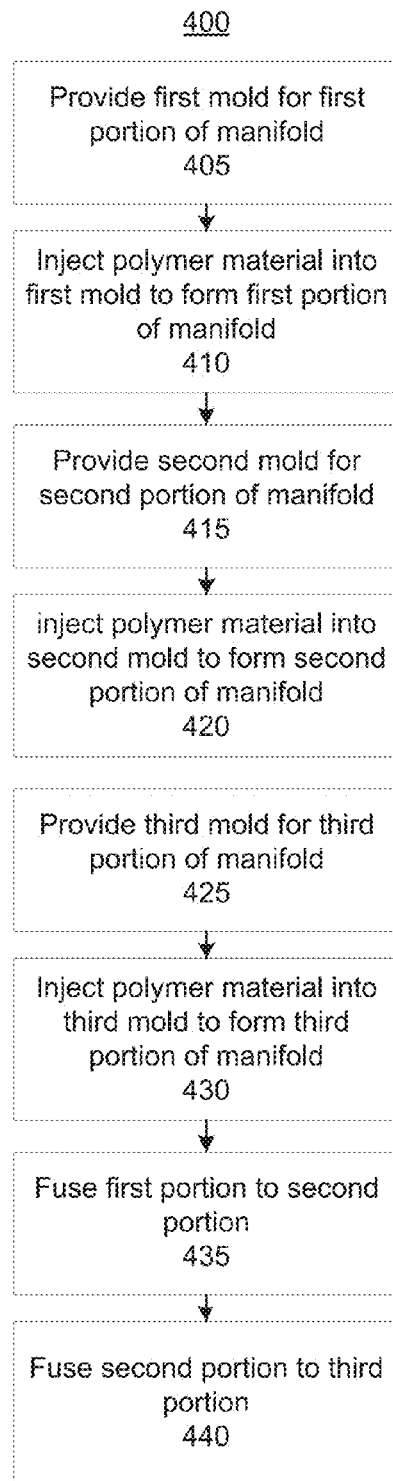
FIG. 4A is a flow diagram of a process for forming a three-dimensional microfluidic manifold, according to an illustrative implementation.

FIG. 4A is a block diagram of a process 400 for forming a three-dimensional microfluidic manifold, according to an illustrative implementation. The process 400 includes providing a first mold for a first portion of a manifold (stage 405). The process 400 includes injecting a polymer material into the first mold to form the first portion of the manifold (stage 410). The process 400 includes providing a second mold for a second portion of the manifold (stage 415). The process 400 includes injecting a polymer material into the second mold to form the second portion of the manifold (stage 420). The process 400 includes providing a third mold for a third portion of the manifold (stage 425). The process 400 includes injecting a polymer material into the third mold to form the third portion of the manifold (stage 430). The process 400 includes fusing the first portion of the manifold to the second portion of the manifold (stage 435). The process 400 includes fusing the second portion of the manifold to the third portion of the manifold (stage 440).

Figure 4B:
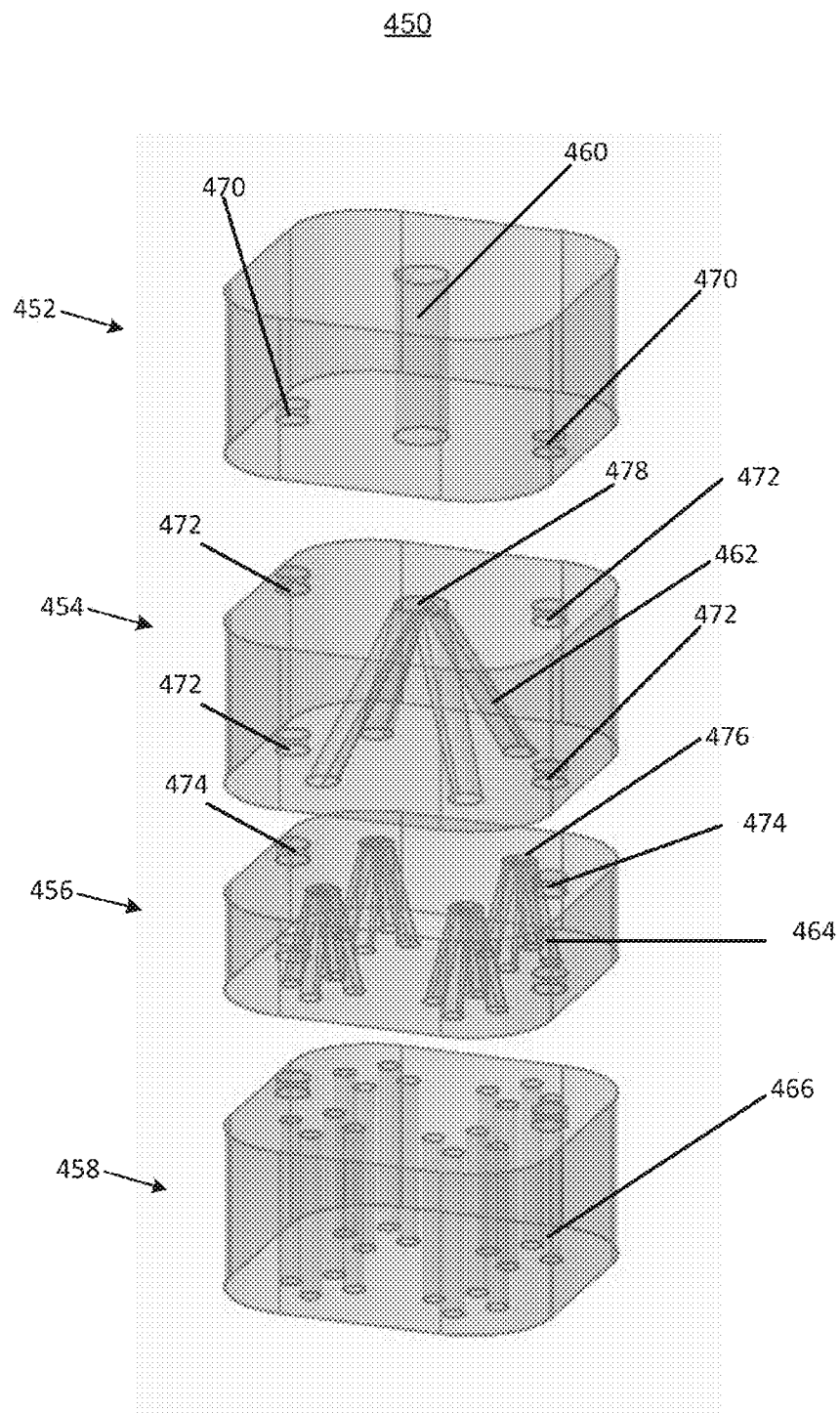
FIG. 4B is a depiction of several example portions of the microfluidic manifold formed through the process shown in FIG. 4A.

FIG. 4B is a depiction of a several example portions of a microfluidic manifold 450 formed through the process 400 shown in FIG. 4A. The portions of the manifold 450 are shown as translucent so that the channels that will form the manifold 450 are visible. However, in some implementations, the portions of the manifold 450 are formed from an opaque material. The process 400 of FIG. 4A will now be described with reference to the manifold portions shown in FIG. 4B.

Referring again to FIG. 4A, the process 400 includes providing a first mold for a first portion of a manifold 450 (stage 405). The first portion can include a primary channel having an inlet and an outlet. The primary channel can be configured to carry fluid in a first direction. The process 400 includes injecting a polymer material into the first mold to form the first portion of the manifold 450 (stage 410). For example, the polymer material injected into the first mold can include polystyrene, polycarbonate, polydimethylsiloxane (PDMS), cyclic olefin copolymer (COC), or other non-degradable polymers. In some implementations, the polymer material may include an additively manufactured resin. The first portion of the manifold 450 is shown as portion 452 in FIG. 4B. The first portion 452 can be formed from a solid material such as plastic or metal that is injection molded using the first mold provided in step 405. The primary channel 460 is shown in FIG. 4B. In some implementations, the polymer material can be flexible so that it can easily be removed from the first mold. In other implementations, the first mold can be dissolvable. For example, the first mold can be made from a dissolvable wax or a photodissolvable polymer. The first mold can then be dissolved around the injected polymer material that forms the first portion 452 of the manifold 450 after the first portion 452 cures. In some implementations, the first portion 452 can also include fiducials 470, which can be configured to facilitate aligning the first portion 452 with another mold portion to assemble the manifold 450.

The process 400 includes providing a second mold for a second portion of the manifold 450 (stage 415). The second portion can include a plurality of secondary channels. Each secondary channel can each have an inlet and an outlet. The inlet of each secondary channel can couple to a first junction 478. In some implementations, the secondary channels are non-coplanar with each other. The secondary channels may be equal or unequal in both length and diameter. In some implementations, the secondary channels may be arranged symmetrically about an axis. For example, the axis can be aligned with the primary channel 460 and the secondary channels can be configured to transport fluid away from the primary channel. The process 400 includes injecting a polymer material into the second mold to form the second portion of the manifold 450 (stage 420). The second portion is shown as portion 454 in FIG. 4B. The second portion 454 can be formed from a solid material such as plastic or metal. The secondary channels, exemplified by secondary channel 462, are also shown in FIG. 4B.

In some implementations, the injected polymer material can be flexible so that the second portions 454 can easily be removed from the second mold. In other implementations, the second mold can be dissolvable. For example, the second mold can be made from a dissolvable wax or a photodissolvable polymer. The second mold can then be dissolved around the injected polymer material that forms the second portion 454 of the manifold 450 after the second portion 454 cures. In some implementations, the second portion 454 can also include fiducials 472, which can be configured to facilitate aligning the second portion 454 with another mold portion to assemble the manifold.

The process 400 includes providing a third mold for a third portion of the manifold 450 (stage 425). The third portion can include a plurality of tertiary channels. Each tertiary channel can each have an inlet and an outlet. The inlet of each tertiary channel can couple to a second junction. In some implementations, the tertiary channels are non-coplanar with each other. The tertiary channels may be equal or unequal in both length and diameter. In some implementations, the tertiary channels can be arranged symmetrically about an axis. For example, the axis can be aligned with one of the secondary channels, such as secondary channel 462, and the tertiary channels can be configured to transport fluid away from the secondary channels. The process 400 includes injecting a polymer material into the third mold to form the third portion of the manifold 450 (stage 430). The third portion is shown as portion 456 in FIG. 4B. The portion 456 can be formed from a solid material such as plastic or metal. The tertiary channels, exemplified by tertiary channel 464, are also shown in FIG. 4B.

In some implementations, the third portion 456 can be configured to form several groups of tertiary channels. Each group can include two or more tertiary channels whose inlets are coupled at a single junction. Each respective group of tertiary channels can be configured to couple to a respective secondary channel. For example, one group of tertiary channels, including tertiary channel 464, has inlets coupled to the junction 476 as shown in FIG. 4B.

In some implementations, the injected polymer material can be flexible so that it can easily be removed from the third mold. In other implementations, the third mold can be dissolvable. For example, the third mold can be made from a dissolvable wax or a photodissolvable polymer. The third mold can then be dissolved around the injected polymer material that forms the third portion 456 of the manifold 450 after the third portion 456 cures. In some implementations, the third portion 456 can also include fiducials 474, which can be configured to facilitate aligning the third portion 456 with another mold portion to assemble the manifold 450.

The process 400 includes fusing the first portion of the manifold 450 to the second portion of the manifold 450 (stage 435). In some implementations, the first portion 452 and second portion 454 can be fused by an adhesive. In other implementations, adjacent surfaces of the first portion 452 and second portion 454 can be heated to melting temperature, brought into contact with each other, and then cooled so that the adjacent surfaces remain fused after the portions are solidified. The fiducials 470 can interlock with the fiducials 472 to ensure that the first portion 454 and second portion 454 of the manifold 450 are properly aligned. For example, the fiducials 470 and 472 can allow the first portion 452 and second portion 454 to be fused such that the outlet of the primary channel 460 couples to the inlets of the secondary channels at the junction 478. Because the secondary channels are configured to be non-coplanar, the secondary channels can transport fluid in various directions away from the direction of the primary channel 460.

The process 400 includes fusing the second portion 454 of the manifold 450 to the third portion 456 of the manifold 450 (stage 440). In some implementations, the second portion 454 and third portion 456 can be fused by an adhesive. In other implementations, adjacent surfaces of the second portion 454 and third portion 456 can be heated to melting temperature, brought into contact with each other, and then cooled so that the adjacent surfaces remain fused after the portions are solidified. The fiducials 472 can interlock with the fiducials 474 to ensure that the second portion 454 and third portion 456 of the manifold 450 are properly aligned. For example, the fiducials 472 and 474 can allow the second portion 454 and third portion 456 to be fused such that the outlet of the secondary channel 462 couples to the inlets of a group of tertiary channels including tertiary channel 464 at the junction 476. The tertiary channels are non-coplanar, and can therefore carry fluid in various directions away from the direction of the secondary channel 462 to which they are fused. In some implementations, there may be a several groups of tertiary channels. Each group can include two or more tertiary channels coupled to a respective junction at their inlets. The process 400 can then include fusing the second portion 454 and third portion 456 such that each group of tertiary channels is coupled to a respective secondary channel at a respective junction.

In some implementations, additional molds may be used to create additional manifold portions to extend the tertiary channels of the manifold 450. For example, the portion 458 can be used to form a plurality of channels, exemplified by channel 466. The portion 458 can then be fused to the portion 456 so that each channel in the portion 458 can be coupled to a respective tertiary channel of the portion 465 to extend the length of the tertiary channels. In some implementations, after the manifold portions have been fused to form the manifold, the junctions at which the channels are coupled can be polished to smooth the inner surfaces of the channels.

Figure 4C:
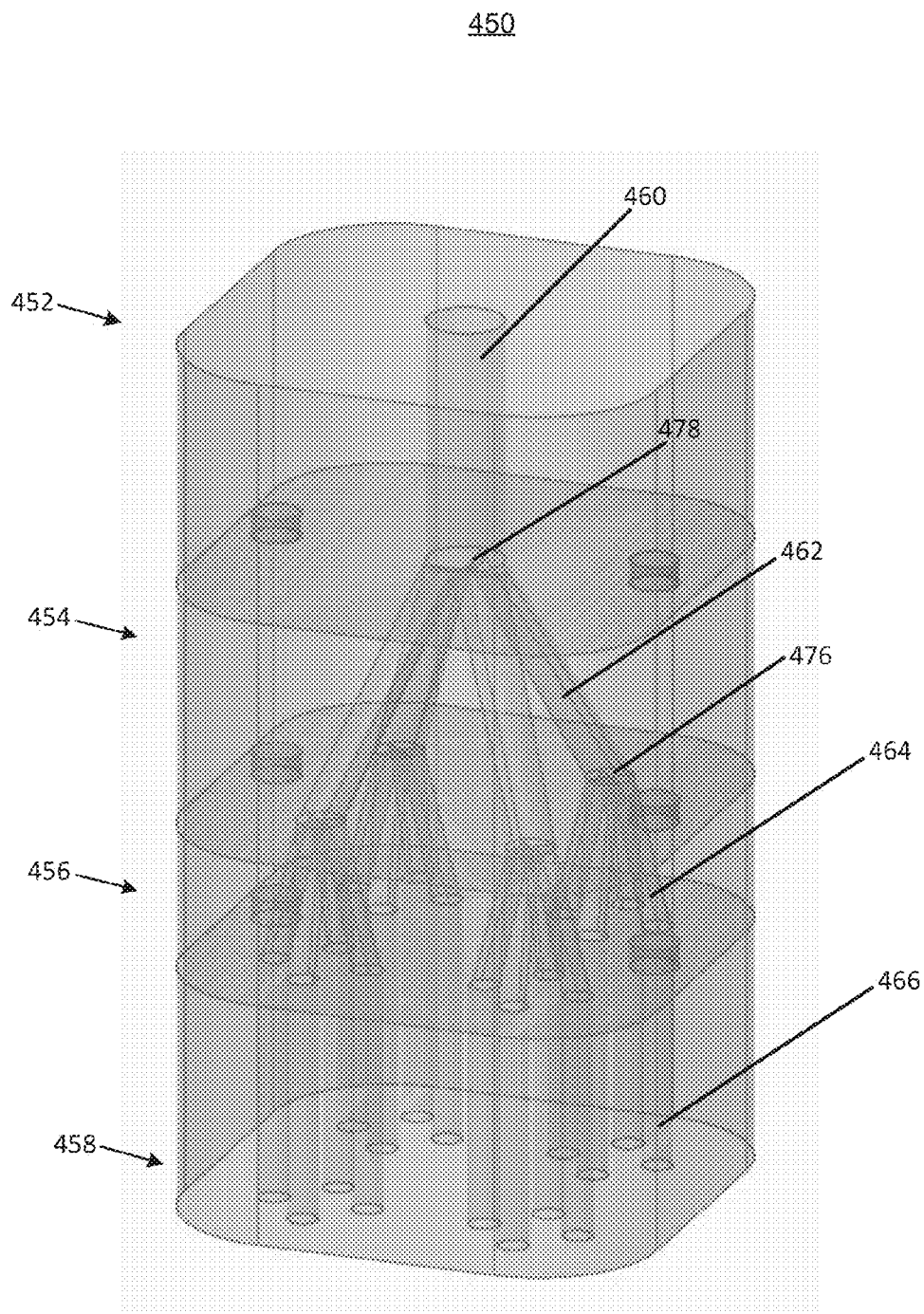
FIG. 4C is a depiction of a three-dimensional microfluidic manifold formed through the process shown in FIG. 4A, according to an illustrative implementation.

FIG. 4C is a depiction of the three-dimensional microfluidic manifold 450 formed through the process 400 shown in FIG. 4A, according to an illustrative implementation. The manifold 450 is shown in its fully assembled condition, with the first portion 452 fused to the second portion 454, and the second portion 454 fused to the third portion 456. The manifold 450 also includes a fourth portion 458 fused to the third portion 456.

As shown, the primary channel 460 couples to the secondary channels at the junction 478. The third portion 456 includes four groups of tertiary channels. Each group of tertiary channels couples to a respective secondary channel at a respective junction. For example, the group of tertiary channels including tertiary channel 464 couples to the secondary channel 462 at the junction 476. The fourth portion 458 of the manifold 450 includes channels that extend the lengths of the tertiary channels. For example, channel 466 extends the length of tertiary channel 464. In some implementations, the microfluidic manifold 450 can be formed using other processes. For example, the manifold 450 can be formed using additive manufacturing techniques such as 3D printing, stereo lithography, or direct metal sintering.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed only in connection with one implementation are not intended to be excluded from a similar role in other implementations.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. A microfluidic device comprising:
a manifold having a first manifold channel, a second manifold channel, and a third manifold channel, coupled to a substrate defining an artificial vasculature, wherein:
the first manifold channel is configured to carry blood in a first direction;
each of the second and third manifold channels couples to the first manifold channel at a first junction and is configured to receive blood from the first manifold channel such that a total blood flow rate through the second and third manifold channels is substantially the same as a blood flow rate through the first manifold channel;
the second manifold channel is configured to carry blood in a second direction away from the first direction;
the third manifold channel is configured to carry blood in a third direction away from the first direction; and
the first, second, and third manifold channels are not arranged to all carry fluid in directions that lie within a common plane, wherein:
at least one of the first manifold channel, the second manifold channel and the third manifold channel further comprises a transition region,
the cross-sectional area of the at least one manifold channel upstream from the transition region such that fluid flowing through the at least one manifold channel downstream from the transition region experiences a higher shear rate than fluid flowing through the at least one manifold channel upstream from the transition region is larger than the cross-sectional area of the at least one manifold channel downstream from the transition region and
the transition region comprises sidewalls that narrow at least one manifold according to one of a Hicks-Henne bump function, a non-uniform rational basis spline, a cubic spline, a T spline, a point cloud, and a polynomial function.

2. The microfluidic device of claim 1, wherein walls of the junction are defined by one of a Hicks-Henne bump function, a non-uniform rational basis spline, a cubic spline, a T spline, a point cloud, and a polynomial function.

3. The microfluidic device of claim 1, wherein:
the first manifold channel is further configured to carry blood at a first wall shear rate;
the second manifold channel is further configured to carry blood at a second wall shear rate, lower than the first wall shear rate; and
the third manifold channel is further configured to carry blood at a third wall shear rate, lower than the first wall shear rate.

4. The microfluidic device of claim 3, wherein the first junction is configured to ensure that a wall shear rate gradient through the junction is maintained below a threshold selected to maintain blood health.

5. The microfluidic device of claim 4, wherein the threshold is about 0.0006 inverse seconds per micron.

6. The microfluidic device of claim 3, wherein the first manifold channel is configured to transport blood at a wall shear rate in the range of about 4500 inverse seconds to about 10,000 inverse seconds.

7. The microfluidic device of claim 3, wherein at least one of the second manifold channel and the third manifold channel is configured to transport blood at a wall shear rate in the range of about 100 inverse seconds to about 800 inverse seconds.

8. The microfluidic device of claim 3, wherein the first wall shear rate is selected to create a driving force sufficient to dislodge blood clots in the manifold.

9. The microfluidic device of claim 1, wherein the transition region is configured to ensure that a wall shear rate gradient through the manifold channel is maintained below about 0.0006 inverse seconds per micron.

10. The microfluidic device of claim 1, further comprising fourth and fifth manifold channels, wherein:
   each of the fourth and fifth manifold channels couples to the second manifold channel at a second junction and is configured to receive blood from the second manifold channel such that a total blood flow rate through the fourth and fifth manifold channels is substantially the same as a blood flow rate through the second manifold channel;
   the fourth manifold channel is configured to carry blood in a fourth direction away from the second direction;
   the fifth manifold channel is configured to carry blood in a fifth direction away from the second direction; and
   the second, fourth, and fifth manifold channels are not arranged to all carry fluid in directions that lie within a common plane.

11. The microfluidic device of claim 10, wherein:
the fourth manifold channel is further configured to carry blood at a fourth wall shear rate, lower than the second wall shear rate; and
   the fifth manifold channel is further configured to carry blood at a fifth wall shear rate, lower than the second wall shear rate.

12. The microfluidic device of claim 1, wherein the transition region is configured to change the wall shear rate experienced by blood transported through the at least one channel such that the wall shear rate experienced by blood upstream from the transition region is lower than a wall shear rate experienced by blood downstream from the transition region.

13. The microfluidic device of claim 12, wherein a length of the transition region is selected to achieve a desired wall shear rate gradient in the transition region.

14. The microfluidic device of claim 13, wherein the length of the transition region is inversely proportional to the wall shear rate gradient in the transition region.

15. The microfluidic device of claim 1, wherein the manifold further comprises sixth and seventh manifold channels that converge at a third junction to form an eighth manifold channel, such that a blood flow rate through the eighth channel is substantially the same as a total blood flow rate through the sixth and seventh manifold channels, and wherein:
   the sixth channel is configured to transport blood at a sixth wall shear rate;
   the seventh channel is configured to transport blood at a seventh wall shear rate; and
   the eighth channel is configured to transport blood at an eighth wall shear rate, lower than both the sixth and seventh wall shear rates.

* * * * *